(12) United States Patent
Lei et al.

(10) Patent No.: US 8,957,019 B2
(45) Date of Patent: Feb. 17, 2015

(54) OLIGOPEPTIDE FOR TREATING LIVER FIBROSIS AND/OR TREATING HEPATITIS B AND/OR IMPROVING LIVER FUNCTION

(75) Inventors: Haimin Lei, Beijing (CN); Qiang Li, Beijing (CN)

(73) Assignee: Haimin Lei, Beijing (CN)

( * ) Notice: Subject to any disclaimer, the term of this patent is extended or adjusted under 35 U.S.C. 154(b) by 0 days.

(21) Appl. No.: 14/346,087

(22) PCT Filed: Nov. 1, 2011

(86) PCT No.: PCT/CN2011/081620
§ 371 (c)(1),
(2), (4) Date: Mar. 20, 2014

(87) PCT Pub. No.: WO2013/063755
PCT Pub. Date: May 10, 2013

(65) Prior Publication Data
US 2014/0221275 A1    Aug. 7, 2014

(51) Int. Cl.
*A61K 39/29* (2006.01)
*A61K 35/407* (2006.01)
*A61K 38/08* (2006.01)
*C07K 7/06* (2006.01)
*C07K 14/47* (2006.01)
*A61K 38/00* (2006.01)

(52) U.S. Cl.
CPC .. *C07K 7/06* (2013.01); *A61K 38/00* (2013.01)
USPC ........................... 514/4.3; 514/21.7; 530/329

(58) Field of Classification Search
CPC .......... C07K 7/06; C07K 14/47; A61K 39/29; A61K 35/407; A61K 38/08
USPC ................................... 514/4.3, 21.7; 530/329
See application file for complete search history.

(56) References Cited

U.S. PATENT DOCUMENTS

2007/0044171 A1 * 2/2007 Kovalic et al. ................ 800/278

OTHER PUBLICATIONS

BAF23834 from GenBank. pp. 1-3. 2004.*
Water is natural product from www.biology-online.org/dictionary/Water, pp. 1-3. Accessed Apr. 24, 2014.*
SEQ ID No. 153557 from US 2007/0044171, 2007.*
Li Yanyan, "Active Oligopeptides Research from Carapax Trionycis Based on CAM Model [D]." M.S. Thesis, Beijing University of Chinese Medicine, 2008, English abstract attached.

* cited by examiner

*Primary Examiner* — Julie Ha
(74) *Attorney, Agent, or Firm* — Nath, Goldberg & Meyer; Tanya E. Harkins; Joshua B. Goldberg (57) ABSTRACT

Disclosed is an oligopeptide for treating liver fibrosis and/or hepatitis B and/or improving liver function. The oligopeptide is obtained by reflux extraction via water, ethanol precipitation and isolation through a cation exchange resin column and a gelatinous resin column from a turtle shell. Pharmaceutically conventional excipients can be added to the oligopeptide prepared according to the present invention to prepare various dosage forms. The oligopeptide has good efficacy in treating liver fibrosis and improving liver function.

3 Claims, 5 Drawing Sheets

Figure 1

Figure 2 blank for control

Figure 3

N terminal G

Figure 11 blank for control

Figure 12

N terminal G

Standard amino acid

SEQUENCE LISTING

```
<160> NUMBER OF SEQ ID NOS: 2

<210> SEQ ID NO 1
<211> LENGTH: 7
<212> TYPE: PRT
<213> ORGANISM: Trionyx  Sinensis  Wiegmann

<400> SEQUENCE: 1

Gly Ala Gly Pro His Gly Gly
1               5

<210> SEQ ID NO 2
<211> LENGTH: 6
<212> TYPE: PRT
<213> ORGANISM: Trionyx  Sinensis  Wiegmann

<400> SEQUENCE: 2

Gly Ala Gly Pro His Gly
1               5
```

OLIGOPEPTIDE FOR TREATING LIVER FIBROSIS AND/OR TREATING HEPATITIS B AND/OR IMPROVING LIVER FUNCTION

This is a National Phase Application filed under 35 U.S.C. 371 as a national stage of PCT/CN2011/081620, filed Nov. 1, 2011, the content of which is hereby incorporated by reference in its entirety.

TECHNICAL FIELD

The present invention relates to oligopeptides, especially relates to oligopeptides isolated from traditional Chinese medicine carapax amydae with the effects of anti- hepatitis B, anti-liver fibrosis and anti-tumor.

"The Sequence Listing submitted in text format (.txt) filed on Mar. 20, 2014, named "QQCN130011_1111213PCT_20131021_SequenceListing.txt", (created on Feb. 7, 2014, 1 KB), is incorporated herein by reference."

BACKGROUND ART

Carapax amydae is from the carapace of Trionychidae animal terrapin Trionyx SinensisWiegmann. It is mainly produced in Hubei, Hunan Province of China et al. and can soften hard lumps and dispel nodes, nourish yin and clear up heat, suppress hyper-yang to eliminate wind. Modern pharmacology researches have shown that it can resist mutation and fatigue, and has immunomodulatory and hepatoprotective effects.

It is well accepted in the documents available nowadays that the main component of carapax amydae is amino acid (Change of chemical components of carapax testudinis and carapax amydae before and after process, Chinese Pharmaceutical Journal, 1989, 24(1):26-28), however, it is not clearly pointed out that the active ingredients of carapax amydae are oligopeptides. We have determined that the main components of carapax amydae are oligopeptides upon experiments researches.

Among the existing literature and techniques at home and abroad, except for the inventor, others have not extracted, isolated and identified the oligopeptide components in carapax amydae.

Among the existing literature and techniques at home and abroad, oligopeptides with the sequences of GAGPHGG and GAGPHG have not been synthesized. Only a large number of synthesis methods for peptides have been reported.

Among the existing literature and techniques at home and abroad, the activity of oligopeptides with sequences of GAGPHGG and GAGPHG have not been reported at all.

SUMMARY OF THE INVENTION

One objective of the present invention is to provide an oligopeptide for resisting hepatitis B and treating liver fibrosis.

Another objective of the present invention is to provide an preparation method for the oligopeptide for resisting hepatitis B and treating liver fibrosis.

Yet another objective of the present invention is to provide a method for treating hepatitis B, liver injury and liver fibrosis though an oligopeptide.

Another objective of the invention is to provide a use of an oligopeptide in the manufacture of pharmaceuticals for treating hepatitis B, liver injury and liver fibrosis.

In the present invention, traditional Chinese medicine carapax amydae was used as the research object. A variety of technologies and methods of chemical analysis, isolation and identification are used in order to systemically isolate and identify the peptides components of carapax amydae. Liquid phase peptide synthesis technology was used to completely synthesize monomers of oligopeptides, and hepatitis B model of duck, CCL4 acute liver injury model of mice, CCL4 liver fibrosis model of rats and S180 solid tumor bearing model of chicken and mice were used to determine the activity of the monomers of oligopeptides in order to seek the lead compound in the oligopeptides for anti-hepatitis B, anti-liver fibrosis and anti-tumor.

To achieve the objectives of the above-mentioned invention, scheme 1 or scheme 2 can be selected as follows.

Scheme 1:

The present invention provides an oligopeptide for resisting hepatitis B virus, treating or preventing liver fibrosis, SEQ ID NO: 1 of which is Gly-Ala-Gly-Pro-His-Gly-Gly.

The oligopeptide with SEQ ID NO: 1 is a white amorphous powder, its biuret reaction is positive, and it easily dissolves in water and hardly dissolves in non-polar solvents such as ethyl acetate, acetone, chloroform, and so on. The amino acid sequence thereof was analyzed by ESI-MS(M/e) and the following result was obtained: 551(GAGPHGG), 494(AG-PHGG), 423(GPHGG), 366(PHGG), 269(HGG), 132(GG), 75(G) and 478(GAGPHG), 421(GAGPH), 284(GAGP), 187(GAG), 130(GA), 59(G+H- OH).

The oligopeptide with SEQ ID NO: 1 can be L-type amino acid or D-type amino acid.

The present invention provides a preparation method for the oligopeptide with SEQ ID NO: 1, which is isolating the oligopeptide with SEQ ID NO: 1 from carapax amydae.

Said preparation method for the oligopeptide with SEQ ID NO: 1 comprises the following steps:

Step 1: water being added into the crude powder of carapax amydae, and then reflux extraction and concentration are carried out in order to obtain concentrated solution;

Step 2: alcohol being added into the concentrated solution from step 1 in order to carry out alcohol precipitation, and then alcohol precipitate product being obtained;

Step 3: the alcohol precipitate product from step 2 being isolated/detected, and an oligopeptide with SEQ ID NO: 1 being collected.

As for the above mentioned preparation method for the oligopeptide with SEQ ID NO: 1, the alcohol precipitation in step 2 is preferably carried out for 2-4 times, and the concentration of ethanol in every alcohol precipitation is from low to high.

In the isolation of step 3, cation exchange resin is used firstly for isolation, and then gel column chromatography is carried out;

In the detection of step 3, high-performance liquid chromatography (HPLC) method can be used for detection and electro-spray ionization-mass spectrometry (ESI-MS) can be used for identification.

As for the preparation method for the oligopeptide with the above mentioned SEQ ID NO: 1, the step 2 is that ethanol is added into the concentrated solution until the concentration of alcohol is 20%, then the solution is centrifuged and ethanol is added into the supernatant liquid until the concentration of alcohol is 60%. The solution is centrifuged again, and ethanol is added into the supernatant until the concentration of alcohol is 80%.

As for the preparation method for the oligopeptide with the above mentioned SEQ ID NO: 1, the step 3 is preferably as follows: the alcohol precipitate product is dissolved, and then cation exchange resin is used firstly for isolation, and then Sephadex LH-20 gel column chromatography is carried out. Next, HPLC detection is carried out and the oligopeptide with SEQ ID NO: 1 is collected.

As for the preparation method for the oligopeptide with above mentioned SEQ ID NO: 1, the step 3 is as follows: the alcohol precipitate product which is obtained by 80% alcohol is dissolved in water, and then eluted on cation exchange resin by buffers of pH 4-5, the fractions, biuret reagent reaction of which is positive, are collected and combined, then freeze dried and dissolved in water; next, the solution is then passed through a Sephadex LH-20 gel column, eluted by pure water, the fractions, chromatographic peak of which is single by HPLC detection, are collected and combined, and then freeze dried, finally the oligopeptide with SEQ ID NO: 1 is collected.

As for the preparation method for the oligopeptide with above mentioned SEQ ID NO: 1, in step 1, 6-10 times amount of water is added to the crude powder of carapax amydae (made by vinegar), reflux extraction is carried out for 1-3 times, every time for 1-2h, and the extraction liquid is condensed until the relative density thereof is 1.1-1.13.

The present invention further provides a preparation method for the oligopeptide with SEQ ID NO: 1, wherein liquid phase synthesis is used for obtaining the oligopeptide.

The present invention further provides a preparation method for the oligopeptide with SEQ ID NO: 1, wherein solid phase synthesis is used for obtaining the oligopeptide.

The step of identifying the sequence of said oligopeptide is as follows.

1. Biuret reaction is used for chemical identification, and then the solubility in a solvent such as water, ethyl acetate, acetone, chloroform and the like is respectively assessed;

2. The molecular weight of the oligopeptide is determined, ESI-MS:574(M+Na), 552(M+H) ;

3. The types of amino acids are initially identified by TLC on silica gel;

4. Electro-spray ionization mass spectrometry (ESI-MS) and amino acid automatic analyzer are used for analysis, and amino acid sequences of two kinds of oligopeptides are obtained.

The present invention provides pharmaceutical composition of the oligopeptide with SEQ ID NO: 1 in any convenient dosage form, including oral form or parenteral form. They are especially suitable to be prepared as injection form.

Pharmaceutically ordinary excipients can be added into the oligopeptide with SEQ ID NO: 1 in order to obtain a variety of dosage forms, including injection form, tablet form (matrix tablet, coated tablet, dispersible tablet and so on), capsule form, sustained release agent, controlled release agent, liposome and the like.

In order to obtain such dosage forms, pharmaceutically acceptable excipients, such as solvent, bulking agent, disintegrant, lubricant, suspending agent, binding agent, edulcorant, corrigent, preservative, matrix, and so on, should be added when preparing those dosage forms. The solvent includes water for injection, glycerine, polyethyleneglycol; the bulking agent includes starch, amylum pregelatinisatum, lactose, mannitol, chitin, microcrystalline cellulose, sucrose and so on; the disintegrant includes starch, amylum pregelatinisatum, microcrystalline cellulose, sodium carboxymethyl starch, crosslinked polyvinylpyrrolidone, low substituted hydroxypropylcellulose, crosslinked carboxymethylcellulose sodium and so on; the lubricant includes magnesium stearate, sodium dodecyl sulphate, talcum powder, silicon dioxide and so on; the suspending agent includes polyvinylpyrrolidone, microcrystalline cellulose, sucrose, agar, hydroxypropyl methylcellulose and son on; the binding agent includes starch paste, polyvinylpyrrolidone, hydroxypropyl methylcellulose and so on; the edulcorant includes saccharin sodium, aspartame, sucrose, sodium cyclamate, enoxolone and so on; the corrigent includes edulcorants and all kinds of essences; the preservative includes parabens, benzoic acid, sodium benzoate, sorbic acid and salts thereof, benzalkonium bromide, chlorhexidinie acetate, oleum eucalypti and so on; the matrix includes PEG6000, PEG4000, insect wax and so on.

The invention further provides a method for resisting hepatitis B and liver fibrosis, which comprises administering SEQ ID NO: 1 as required in a pharmaceutically acceptable form every day.

The invention further provides a use of SEQ ID NO: 1 in the manufacture of pharmaceuticals for treating liver fibrosis and/or improving liver function.

The invention further provides a use of SEQ ID NO: 1 in the manufacture of pharmaceuticals for resisting hepatitis B virus.

The invention further provides a use of SEQ ID NO: 1 in the manufacture of pharmaceuticals for resisting tumor.

Scheme 2:

The present invention provides an oligopeptide for resisting hepatitis B and liver fibrosis, SEQ ID NO: 2 of which is Gly-Ala-Gly-Pro-His-Gly.

The oligopeptide with SEQ ID NO: 2 is a white amorphous powder, and its biuret reaction is positive, it easily dissolves in water and hardly dissolves in non-polar solvents such as ethyl acetate, acetone, chloroform, and so on. The amino acid sequence thereof was analyzed by ESI-MS, and was confirmed by the following data, ESI-MS(M/e):494(GAGPHG), 423(AGPHG), 366(GPHG), 269(PHG), 132(HG), 75(G) and 421(GAGPH), 284(GAGP), 187(GAG), 130(GA), 59(G+H-OH).

The oligopeptide with SEQ ID NO: 2 can be L-type amino acid or D-type amino acid.

The present invention provides a preparation method for the oligopeptide with SEQ ID NO: 2, which is isolating the oligopeptide with SEQ ID NO: 2 from carapax amydae.

Said preparation method for the oligopeptide with SEQ ID NO: 2 comprises the following steps:

Step 1 : water being added to the crude powder of carapax amydae, and then reflux extraction and concentration being carried out in order to obtain a concentrated solution;

Step 2: alcohol being added into the concentrated solution from step 1 in order to carry out alcohol precipitation, and then alcohol precipitate product being obtained;

Step 3: the alcohol precipitate product from step 2 being isolated, detected, and an oligopeptide with SEQ ID NO: 2 being collected.

As for the preparation method for the oligopeptide with SEQ ID NO: 2, the alcohol precipitation in step 2 is preferably carried out for 2-4 times, the concentration of ethanol in every alcohol precipitation is from low to high.

In the isolation of step 3, cation exchange resin is used firstly for isolation, and then gel column chromatography is carried out;

In the detection of step 3, high-performance liquid chromatography (HPLC) method can be used for detection and electro-spray ionization-mass spectrometry (ESI-MS) can be used for identification.

As for the preparation method for the oligopeptide with above mentioned SEQ ID NO: 2, the step 2 is that ethanol is added into the concentrated solution until the concentrate of alcohol is 20%, then the solution is centrifuged and ethanol is added into the supernatant liquid until the concentrate of alcohol is 60%, next, the solution is centrifuged again, and ethanol is added into the supernatant until the concentrate of alcohol is 80%.

As for the preparation method for the oligopeptide with the above mentioned SEQ ID NO: 2, the step 3 is preferably as follows: the alcohol precipitate product is dissolved, and then cation exchange resin is used firstly for isolation, and then Sephadex LH-20 gel column chromatography is carried out. Next, HPLC detection is carried out and the oligopeptide with SEQ ID NO: 2 is detected.

As for the preparation method for the oligopeptide with above mentioned SEQ ID NO: 2, the step 3 is as follows: the alcohol precipitate product which is obtained by alcohol with concentration of 80% is dissolved in water, and then eluted on cation exchange resin by buffers of pH 4-5, the fractions, biuret reagent reaction of which is positive, are collected, combined, then freeze dried and dissolved in water; next, the obtained solution is then passed through a Sephadex LH-20 gel column, and eluted by pure water, the fractions, chromatographic peak of which is single by HPLC detection, are collected and combined, and then freeze dried to obtain the oligopeptide with SEQ ID NO: 2.

As for the preparation method for the oligopeptide with above mentioned SEQ ID NO: 2, in step 1, 6-10 times amount of water is added to the crude powder of carapax amydae (made by vinegar), reflux extraction is carried out for 1-3 times, each time for 1-2h, and the extraction liquid is condensed until the relative density thereof is 1.1-1.13.

The oligopeptide with SEQ ID NO: 2 is identified as follows:

1. Biuret reaction is used for chemical identification, and then the solubility in solvent such as water, ethyl acetate, acetone, chloroform and the like is assessed;
2. The molecular weight of oligopeptide is determined, ESI-MS:517(M+Na), 495(M+H);
3. The types of amino acids are initially identified by TLC on silica gel;
4. Electro-spray ionization mass spectrometry (ESI-MS) and amino acid automatic analyzer are used for analysis, and amino acid sequences of two kinds of oligopeptides are obtained.

The present invention further provides a preparation method for the oligopeptide with SEQ ID NO: 2, in which liquid phase synthesis is used for obtaining the oligopeptide.

The present invention further provides a preparation method for the oligopeptide with SEQ ID NO: 2, in which solid phase synthesis is used for obtaining the oligopeptide.

The present invention provides pharmaceutical compositions of the oligopeptide with SEQ ID NO: 2 in any convenient dosage form, including oral form or parenteral form. They are especially suitable to be prepared as injection form.

Pharmaceutically ordinary excipients can be added to into the oligopeptide with SEQ ID NO: 2 in order to obtain a variety of dosage forms, including injection form, tablet form (matrix tablet, coated tablet, dispersible tablet, and so on), capsule form, microemulsions, sustained release agent, controlled release agent, liposome, as well as granules, suppositories and liquid preparations such as oral formulation.

In order to obtain such dosage forms, pharmaceutically acceptable excipients, such as solvent, bulking agent, disintegrant, lubricant, suspending agent, binding agent, edulcorant, corrigent, preservative, matrix, and so on, should be added when preparing those dosage forms. The solvent includes water for injection, glycerine, polyethyleneglycol; the bulking agent includes starch, amylum pregelatinisatum, lactose, mannitol, chitin, microcrystalline cellulose, sucrose, and so on; the disintegrant includes starch, amylum pregelatinisatum, microcrystalline cellulose, sodium carboxymethyl starch, crosslinked polyvinylpyrrolidone, low substituted hydroxypropylcellulose, crosslinked carboxymethylcellulose sodium, and so on; the lubricant includes magnesium stearate, sodium dodecyl sulphate, talcum powder, silicon dioxide, and so on; the suspending agent includes polyvinylpyrrolidone, microcrystalline cellulose, sucrose, agar, hydroxypropyl methylcellulose, and so on; the binding agent includes starch paste, polyvinyl pyrrolidone, hydroxypropyl methylcellulose, and so on; the edulcorant includes saccharin sodium, aspartame, sucrose, sodium cyclamate, enoxolone, and so on; the corrigent includes edulcorants and all kinds of essences; the preservative includes parabens, benzoic acid, sodium benzoate, sorbic acid and salts thereof, benzalkonium bromide, chlorhexidinie acetate, oleum eucalypti, and so on; the matrix includes PEG6000, PEG4000, insect wax, and so on.

The invention further provides a method for resisting hepatitis B and liver fibrosis, which method comprises administering SEQ ID NO: 2 as required in a pharmaceutically acceptable form every day.

The invention further provides a use SEQ ID NO: 2 in the manufacture of pharmaceuticals for treating liver fibrosis and/or improving liver function.

The invention further provides a use of SEQ ID NO: 2 in the manufacture of pharmaceuticals for resisting hepatitis B.

The invention further provides a use of SEQ ID NO: 2 in the manufacture of pharmaceuticals for resisting tumor.

DESCRIPTION OF DRAWINGS

FIGS. 3-11: the pattern of the amino acid sequence of oligopeptide compound 1 from amino acid analyzer.

FIGS. 12-19: the pattern of the amino acid sequence of oligopeptide compound 2 from amino acid analyzer.

DETAILED DESCRIPTION OF THE PREFERRED EMBODIMENT

The following are examples of the compounds of the present invention, however, they should not be regarded as the limitation of the scope of the present invention.

Example 1 Identification, extraction, isolation and purification of chemical oligopeptides ingredient in carapax amydae 1. The identification of peptides in carapax amydae-biuret reaction 1.1 equipment and reagents DK-98-I type thermostatic water bath pot; RE-52A type rotatory evaporator; SHB-III type circulation water type multifunctional vacuum pump; the carapax amydae material, which is bought from China TongRenTang drugstore, and identified as the carapace of Trionychidae animal terrapin Trionyx Sinensis Wiegman by LIUChunshen, who is a professor of school of Chinese medicine, Beijing University of Chinese Medicine); cation exchange resin and Sephadex LH-20, both imported package, and the chemical agents used being all analytical pure.

1.2 methods and results 2 ml of water extraction of carapax amydae was added into a tube, then diluted with water to 5 ml, and one drop of 4% NaOH solution and one drop of 1% CuSO4 solution were added. Then the solution was shaken to obtain a uniform solution, the blank control was used in parallel, and coloration was observed. The coloration of carapax amydae water extraction solution was blue-violet.

1.3 conclusions

The biuret reaction of carapax amydae water extraction solution was positive, which indicates that carapax amydae does contain peptides compound.

2. Extraction, isolation and purification of oligopeptide compounds in carapax amydae.

2.1 equipments and reagents (the same as those of 1.1)

Figure 1:
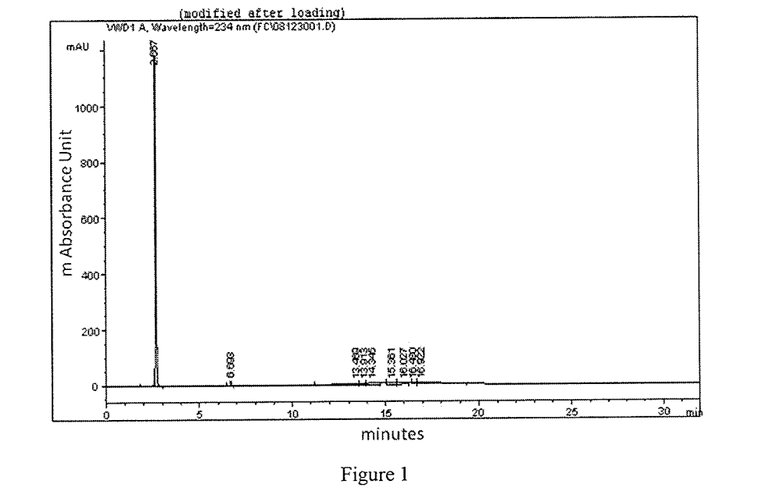
FIG. 1 : a liquid phase figure of oligopeptide compound 1.
Figure 2:
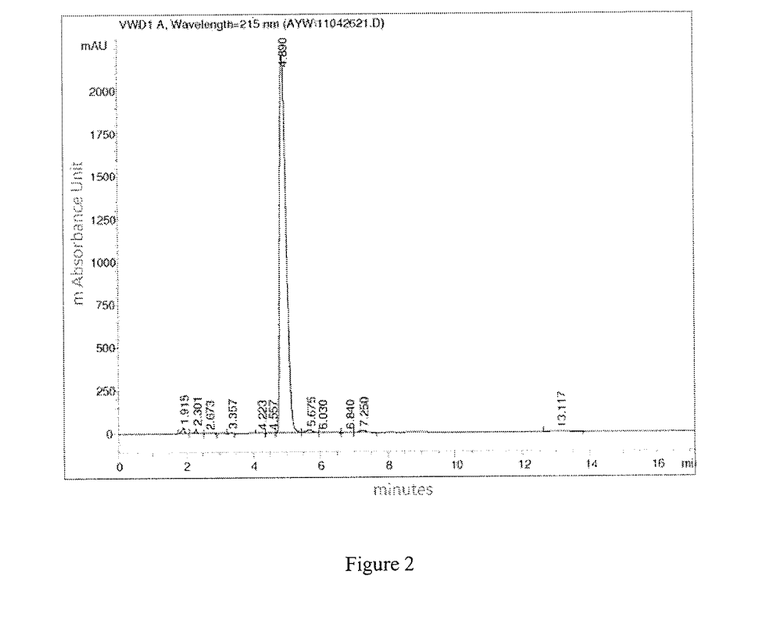
FIG. 2 : a liquid phase figure of oligopeptide compound 2.
Figure 3:
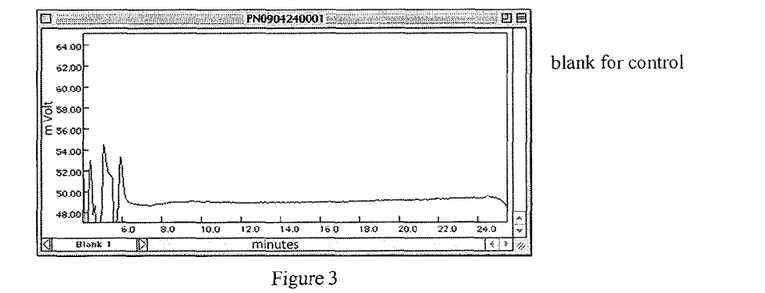
FIG. 3: the pattern of blank for control.
Figure 4:
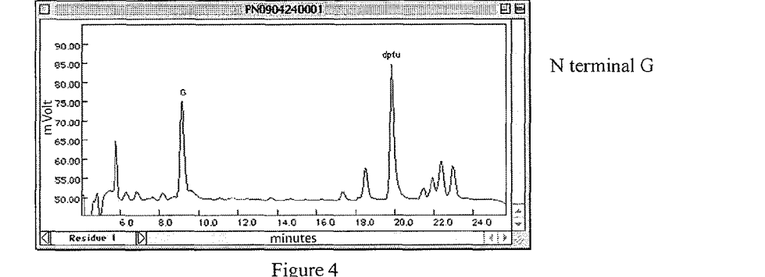
FIG. 4: N-terminal glycine analysis pattern.
Figure 5:
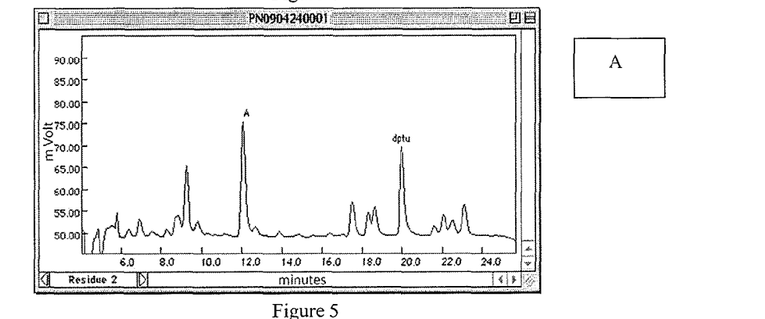
FIG. 5: N-terminal alanine analysis pattern.
Figure 6:
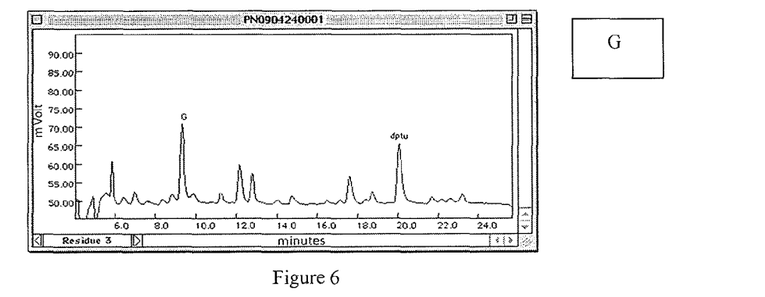
FIG. 6: N-terminal glycine analysis pattern.
Figure 7:
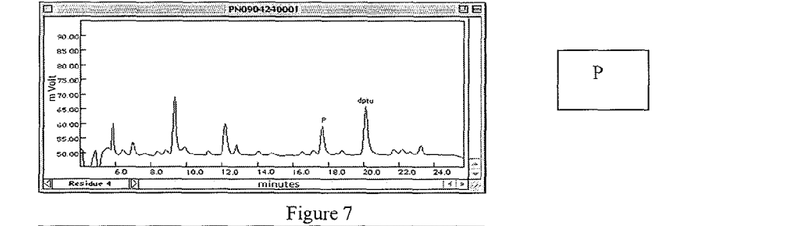
FIG. 7: N-terminal proline analysis pattern.
Figure 8:
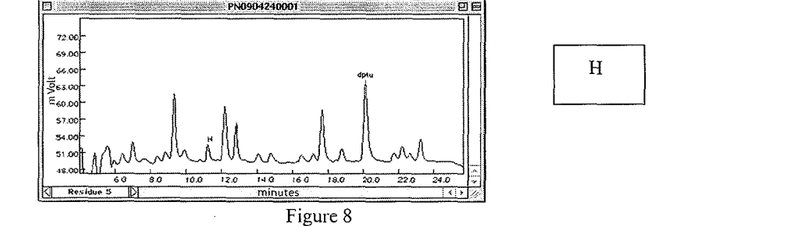
FIG. 8: N-terminal histidine analysis pattern.
Figure 9:
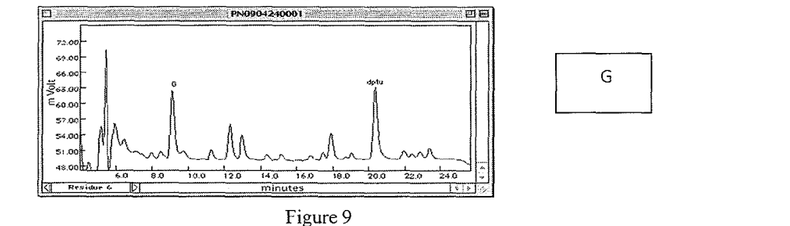
FIG. 9: N-terminal glycine analysis pattern.
Figure 10:
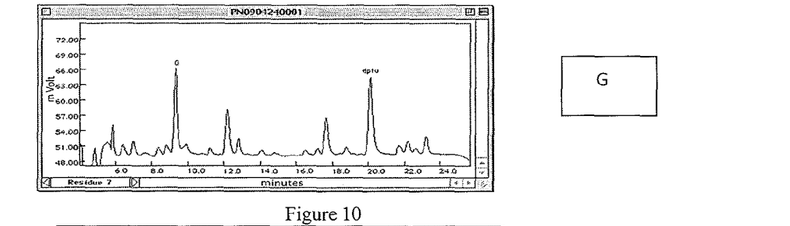
FIG. 10: N-terminal glycine analysis pattern.
Figure 11:
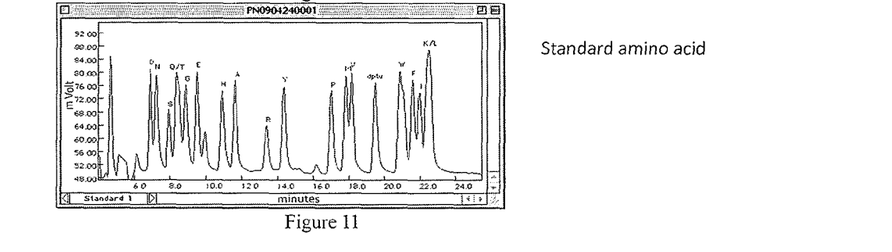
FIG. 11: the pattern of standard amino acid sequence.
Figure 12:
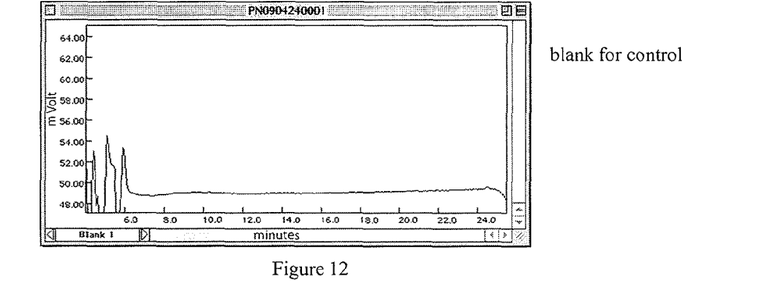
FIG. 12: the pattern of blank for control.
Figure 13:
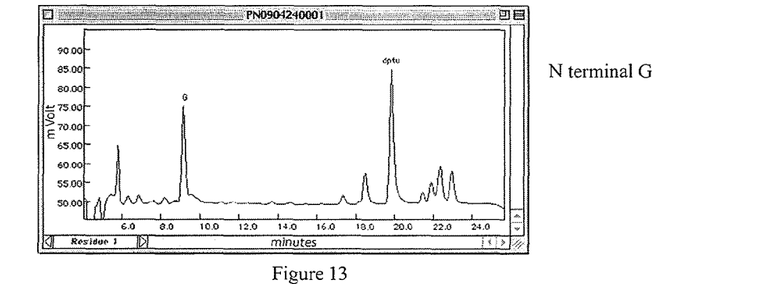
FIG. 13: N-terminal glycine analysis pattern.
Figure 14:
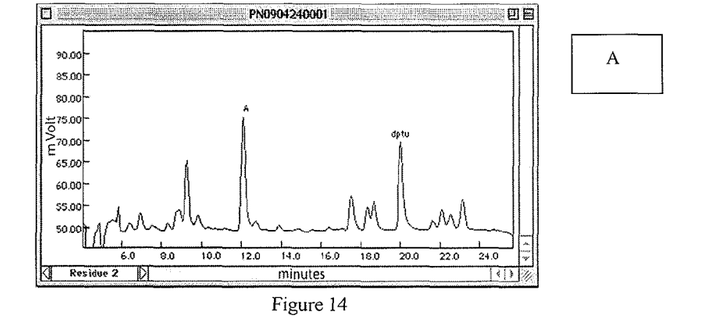
FIG. 14: N-terminal alanine analysis pattern.
Figure 15:
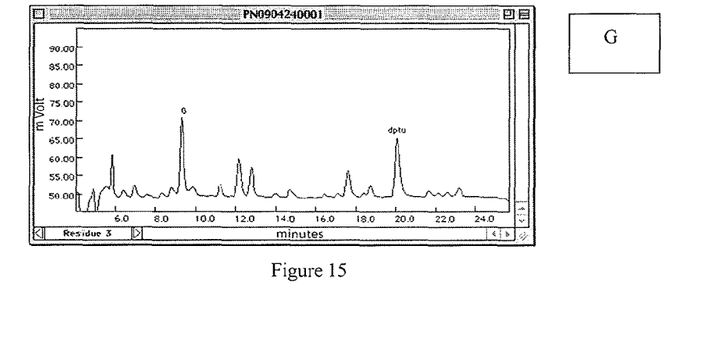
FIG. 15: N-terminal glycine analysis pattern.
Figure 16:
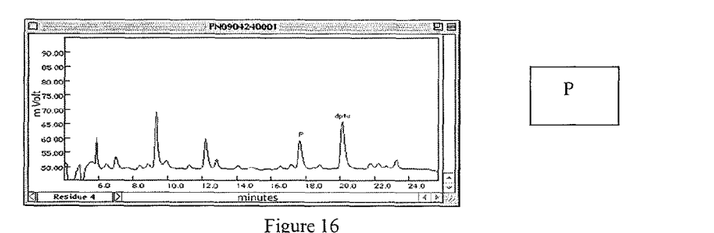
FIG. 16: N-terminal proline analysis pattern.
Figure 17:
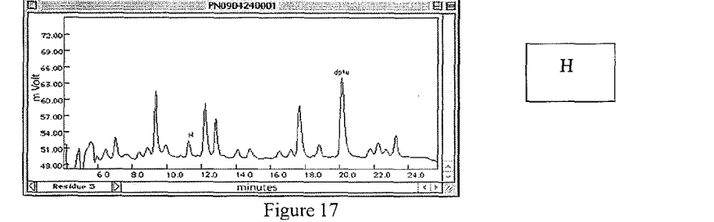
FIG. 17: N-terminal histidine analysis pattern.
Figure 18:
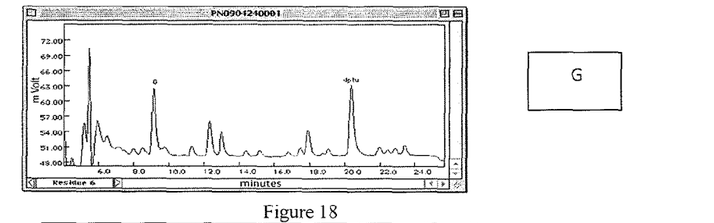
FIG. 18: N-terminal glycine analysis pattern.
Figure 19:
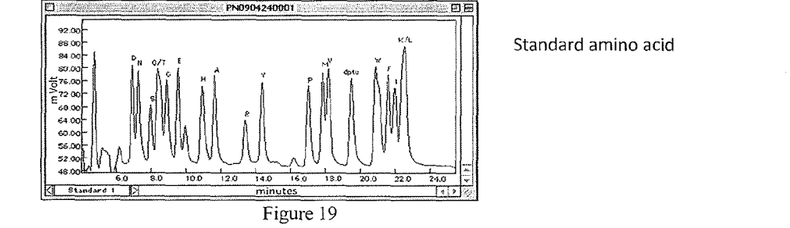
FIG. 19: the pattern of standard amino acid sequence.

2.2 extraction, isolation and purification 200 g crude powder (1 mm±0.1 mm) of carapax amydae was taken and 2000 ml distilled water was added for reflux extraction for 3 times, each time for 2 hours. Extraction solution was condensed to the relative density of 1.1-1.13, and ethanol was added until the alcohol concentration was 20%, 60% and 80% sequentially; the alcohol precipitate product from the solution with the alcohol concentration of 80% was dissolved by 20 ml water or completely dissolved, and then eluted on cation exchange resin by buffers of pH 4-5(5% NaAC solution, adjusted to pH 4.5 by HAc). The fractions which were positive in biuret reaction were collected and combined, and then freeze dried and dissolved in water. The obtained solution is then passed through with the eluent of pure water on a Sephadex LH-20 gel column for chromatograpthy. The single fraction with the retention time of 2.67 minutes detected by HPLC (HPLC detecting conditions is given as follows: chromatographic column: SB-C18 (5 pm, 4.6×250 mm), flow rate: 1.0 ml/min; wave length for UV detection: 234 nm, 210 nm; sample size: 10 μL; column temperature: 35° C., mobile phase: 5% acetonitrile-0.1% trifluoroacetic acid aqueous solution) was collected and combined, then freeze dried to obtain the oligopeptide compound 1 (20 mg) (FIG. 1). The single fraction with the retention time of 4.89 min was collected and combined, then freeze dried to obtain the oligopeptide compound 2 (10 mg) (FIG. 2).

Example 2 Identification of oligopeptides GAGPHGG and GAGPHG

1. Materials and equipment

Compound 1 (self made), the purity determined by HPLC normalization method was more than 98%;

Compound 2 (self made), the purity determined by HPLC normalization method was more than 98%;

Agilent 1100 LC-MSD series trap (double high-pressure solvent pump, on-line vacuum degasser, automatic sampler, column incubator, DAD detector, ESI ion trap mass spectrometric detector, Agilent Ltd. USA);

Amino acid automatic analyzer (ABI PROCISETM492cLC);

Trifluoroacetic acid (TFA, Sigma Ltd. USA), acetonitrile (chromatographic pure, fisher Ltd.), hydrochloric acid (analytical pure).

2. Identification

Compound 1: some of the white amorphous powder prepared in example 1 was used for test. The biuret reaction was positive, and the sample was soluble in water and hardly soluble in non-polar solvents such as ethyl acetate, acetone, chloroform and so on. ESI-MS:574(M+Na), 552(M+H). The determination of the types of amino acids: after being hydrolyzed by concentrated HCl, the product was detected by silica gel thin layer chromatography (condition: silica gel G plate, n-butanol-glacial acetic acid-ethanol-water (4:1:1:2) was used as the developing agent. The sample was developed on the plate and taken out, open-air dried, sprayed with 0.5% ninhydrin acetone solution, and heated at 105° C. until the coloration of the spots was clear). The types of amino acids of compound 1 were determined as glycine(G), alanine(A), proline(P) and histidine(H) after comparing with the standard amino acid (glycine(G), alanine(A), proline(P) and histidine (H)) developed on the same plate. The amino acid sequence analysis was obtained by using automatic amino acid analyzer (FIGS. 3-11), the result of the sequence analysis test was GAGPHGG. The amino acid sequence was further verified by ESI-MS as follows. ESI-MS (M/e): 551(GAGPHGG), 494 (AGPHGG), 423(GPHGG), 366(PHGG), 269(HGG), 132(GG), 75(G) and 478(GAGPHG), 421(GAGPH), 284(GAGP), 187(GAG), 130(GA), 59(G+H-OH), wherein the condition of mass spectroscopy was: Mass Rang Mode: Ultra Scan, Ion Polarity: positive, Ion Source Type: ESI, Dry Temp: 350, Nebulizer: 50.00psi, Dry Gas: 10.001/min.

Compound 2 : it is white amorphous powder. The biuret reaction was positive, and the sample was soluble in water and hardly soluble in non-polar solvents such as ethyl acetate, acetone and chloroform and so on. ESI-MS:517 (M+Na), 495(M+H). The determination of the types of amino acids: after being hydrolyzed by concentrated HCl, the product was detected by silica gel thin layer chromatography (condition: silica gel G plate, n-butanol-glacial acetic acid-ethanol-water (4:1:1:2) was used as the developing agent. The sample was developed on the plate and taken out, open-air dried, sprayed with 0.5% ninhydrin acetone solution, and heated at 105° C. until the coloration of the spots was clear). The types of the amino acids of compound 2 was determined as glycine(G), alanine(A), proline(P) and histidine(H) after comparing with the standard amino acid (glycine(G), alanine(A), praline(P) and histidine(H)) developed on the same plate. The amino acid sequence analysis was obtained by using amino acid automatic analyzer (FIGS. 12-19), the result was GAGPHG. The amino acid sequence of compound 2 was further analyzed by ESI-MS as follows: ESI-MS (M/e):494(GAGPHG), 423(AGPHG), 366(GPHG), 269(PHG), 132(HG), 75(G) and 421(GAGPH), 284(GAGP), 187(GAG), 130(GA), 59(G+H-OH), wherein the condition of MS was: Mass Rang Mode :Ultra Scan, Ion Polarity :positive, Ion Source Type :ESI, Dry Temp :350, Nebulizer :50.00psi, Dry Gas : 10.001/min.

Example 3 Synthesis of oligopeptides GAGPHGG and GAGPHG

1. Materials and equipment Preparative liquid chromatograph; lyophilizer; RE-52A type rotatory evaporator; SHB-III type multifunctional vacuum pump by circulating water;

Agilent 1100 LC-MSD series trap (double high-pressure solvent pump, on-line vacuum degasser, automatic sampler, column incubator, DAD detector, ESI ion trap mass spectrometric detector, Agilent Ltd. USA);

Amino acid automatic analyzer (ABI PROCISETM492cLC); WANG resin (Tianjin Nankai Synthesis Technology Co., Ltd.). Sephadex LH-20 and protected amino acids are both imported package, and the chemical agents used are all analytical pure.

2. Synthesis

See HuangWeide, Polypeptide Synthesis. Science Press, 1985, the part of solid-phase synthesis of the first edition.

2.1 Synthesis of GAGPHGG

Fmoc-G-OH (0.1 mol) (glycine with the amino group protected by 9-fluorenylmethyloxycarbonyl) and HOBT (1-hydroxybenzotriazole) (0.1 mol) was dissolved in dichloromethane (DCM), and DIC (N,N-Diisopropyl carbodiimide) (0.1 mol) was added. The obtained mixture was stirred for 10 min, and then swelled Wang resin (0.04 mol) and DMAP (catalytic amount of 4-dimethylaminopyridine) (0.004 mol) were added. Next, the container was sealed and the temperature was controlled at 25° C-28° C. After reacting for 10 h, the reaction was stopped and the reaction solution was removed by filtration. The Wang resin for reaction was then washed with DMF twice, and DMF was removed by filtration; 20%PIP/DMF reagent was used for deprotection for 15-20 min, then the resin was washed several times with DCM; then reagent 1(the preparation was as follows: 0.4 mol Fmoc-G-OH and 0.4 mol HOBT were dissolved in DCM, then 0.1 mol DIC was added and the obtained mixture was stirred for 10 min) and 0.004 mol DMAP were added, and after reacting for 10 h, the reaction was stopped and the reaction solution was removed by filtration. The resin for reaction was then washed with DMF twice, and DMF was removed by filtration.

According to the procedures mentioned above, Fmoc-H-OH, Fmoc-P-OH, Fmoc-G-OH, Fmoc-A-OH and Fmoc-G-OH were synthesized by condensation reaction sequentially. When the synthetic reaction was over, lysate (TFA-thio-anisole-1,2-ethanedithiol-anisole, volume ratio was 205:12.5:7.9:4.6) was added and the mixture was kept from light for reaction for 3 h. After being filtered, the resin was washed with suitable amount of TFA. The filtrate was added to frozen anhydrous diethyl ether and the container was sealed for 3 h of aging. The precipitate was collected by centrifugalization, and washed with suitable amount of frozen anhydrous diethyl ether. The precipitate was then dissolved in water. After desalination with Sephadex LH-20 gel column, the solution was loaded on preparative HPLC and the fraction with a single chromatographic peak was collected and combined, then lyophilized. The yield was 15.5%. The product was analyzed by ESI-MS and the following peaks appeared: 574 (M+Na), 552(M+H), 551(GAGPHGG), 494(AGPHGG), 423 (GPHGG), 366(PHGG), 269(HGG), 132(GG), 75(G) and 478(GAGPHG), 421(GAGPH), 284(GAGP), 187(GAG), 130(GA), 59(G+H-OH). The purity analyzed by HPLC normalization method was 99.0%.

2.2 Synthesis of GAGPHG

Fmoc-G-OH (0.1 mol) and HOBT (0.1 mol) were dissolved in dichloromethane (DCM), and then DIC (0.1 mol) was added. The obtained mixture was stirred for 10 min, and then swelled Wang resin (0.04 mol) and DMAP (0.004 mol) were added. The container was sealed and the temperature was controlled at 25° C-28° C. After reacting for 10 h, the reaction was stopped and the reaction solution was removed by filtrations. The resin for reaction was then washed with DMF twice, and DMF was removed by filtrations; 20%PIP/DMF reagent was used for deprotection for 15-20 min, then the resin was washed with DCM several times; reagent 1 (the preparation method was as follows: 0.4 mol Fmoc-H-OH and 0.4 mol HOBT were dissolved in DCM, then 0.1 mol DIC was added and the mixture was stirred for 10 min) and 0.004 mol DMAP were added, and after reacting for 10 h, the reaction was stopped and the reaction solution was removed by filtrations. The resin for reaction was then washed with DMF twice, and DMF was removed by filtrations.

According to the procedures mentioned above, Fmoc-P-OH, Fmoc-G-OH, Fmoc-A-OH and Fmoc-G-OH were synthesized by condensation reaction sequentially. When the synthetic reaction was over, lysate (TFA- thio-anisole-1,2-ethanedithiol-anisole, volume ratio was 205:12.5:7.9:4.6) was added and the mixture was kept from light for reaction for 3 h. After being filtered, the resin was washed with suitable amount of TFA.

The filtrate was added to frozen anhydrous diethyl ether and the container was sealed for 3 h of aging. The precipitate was collected by centrifugalization, and washed with suitable amount of frozen anhydrous diethyl ether. The precipitate was then dissolved in water. After desalination with Sephadex LH-20 gel column, the solution was loaded on preparative HPLC and the single chromatographic peak fraction was collected and combined, then lyophilized. The yield was 20.5%. The product was analyzed by ESI-MS and the following peaks appeared: ESI-MS: 517(M+Na), 495(M+H), 494 (AGPHGG), 423(GPHGG), 366(PHGG), 269(HGG), 132(GG), 75(G) and 421(GAGPH), 284(GAGP), 187(GAG), 130(GA) and 59(G+H-OH). The purity analyzed by HPLC normalization method was 99.0%.

Example 4 Determination of the anti-DHBV (Duck Hepatitis B Virus) activity of oligopeptide GAGPHGG 1. Materials 1.1 animals: Beijing ducks of one-day-old, purchased from Beijing Qianjin Duck Farms.

1.2 pharmaceuticals: heptapeptide GAGPHGG (self made, >98%); positive drug Lamivudine (Glaxo Wellcome Pharmaceutical Co. Ltd.).

1.3 principal reagents: duck hepatitis B virus DNA(DHBV-DNA), high positive duck serum (taken from Shanghai Sheldrake, kept under -70° C.); a-32p-dCTP (Beijing Furui Biotechnological Engineering Co. Ltd.); nick translation kits (Promega Corporation) ; Sephadex G-50, Ficoll PVP (Swedish Pharmacia company); SDS (Merck); milt DNA, bovine serum albumin (Institute of Biophysics, Chinese Academy of Sciences).

2. Methods 2.1 DHBV infection: Beijing ducks of one-day-old were administered from leg tibia (iv) with high DHBV-DNA positive duck serum. Blood was taken 7 d after infection, followed by the serum being separated and kept at -70° C.

2.2 experiment for pharmaceutical treatment: the DHBV infected ducks were divided into groups randomly, and for the heptapeptide administration groups, 0.5 mg/Kg and 1 mg/Kg were administered by subcutaneous injection, once every two days for 10 d, respectively. As for the virus control group, physiological saline was substituted for drugs. For the positive drug (Lamivudine) group, the drug was administered twice as 50 mg/kg every day for 10 d. Venous blood was taken from the duck leg tibia before administration, on day 5 of administration, on day 10 of administration and 3 d after the administration was stopped. The serum was separated and kept at -70° C. for inspection.

2.3 detecting method: the duck serum for inspection above mentioned was taken and the dynamic level of DHBV-DNA in the serum was detected by simultaneous spotting each batch. DHBV-DNA probe was tagged with 32 p according to the instructions of nick translation kits, and then dot blot hybridization with the duck serum was carried out. The spots on the film were detected by radioautography, and the absorbance (A) (490 nm) was measured. Then density of serum DHBV-DNA was calculated by using the A value of hybridization spots as the level of DHBV-DNA in sample.

2.4 efficacy calculation: the x±s of serum DHBV-DNA levels at different time point for each group was calculated, and it is carried out to compare the states before and after administration for each group by using paired t-test. The inhibition ratio of DHBV-DNA was calculated and the dynamic change of the duck serum DHBV-DNA inhibition ratio for each group was compared. The administration groups were compared with the virus control group by using group t-test. The DHBV-DNA inhibition ratio=(A value before administration-A value after administration)/A value before administration×100%.

3. Results The semi-quantitative results of the duck serum DHBV-DNA levels for each group wherein ducks were infected with DHBV 2 DNA before and after the administration are shown in table 1. Compared with the virus control group, the duck serum DHBV-DNA level for low dosage group (0.5 mg/kg) does not decline significantly after administration. The duck serum DHBV-DNA inhibition ratio of high dosage group(1 mg/kg) increased significantly 10 d after the administration and 3 d after the administration was stopped, compared with the virus control group, and the level of duck serum DHBV-DNA declined consistently after the administration was terminated.

TABLE 1 influences of the heptapeptide on duck serum DHBV-DNA level of ducks
infected with DHBV (x ± s, n = 6)

| groups | dosage mg/kg | A (before administration) | A (5 d after administration) | A (10 d after administration) | A (3 d after administration was terminated) | Inhibition ratio % 5 d after administration | inhibition ratio % 10 d after administration | inhibition ratio % 3 d after administration was terminated |
|---|---|---|---|---|---|---|---|---|
| control | — | 1.083 ± 0.24 | 1.158 ± 0.16 | 1.248 ± 0.20 | 1.328 ± 0.18 | −6.93 | −15.24 | −22.62 |
| heptapeptide | 0.5 | 1.286 ± 0.12 | 1.239 ± 0.16 | 1.198 ± 0.18 | 1.184 ± 0.19 | 3.65 | 6.84 | 7.93 |
|  | 1 | 1.274 ± 0.14 | 1.204 ± 0.21 | 0.893 ± 0.13** | 0.884 ± 0.16** | 5.49 | 29.91** | 30.61** |
| Lamivudine | 50 | 1.362 ± 0.18 | 1.275 ± 0.09 | 0.696 ± 0.23** | 1.216 ± 0.26** | 6.39 | 48.90** | 10.72** |

Compared with control group, ** P < 0.01

4. Conclusions

Heptapeptide GAGPHGG (1 mg/kg) can inhibit duck hepatitis B virus to some extent.

Example 5 Protection of oligopeptide GAGPHGG for the acute liver injury of mice

1. Materials 1.1 animals: healthy Kunming mice (about 20 g, Beijing Vital River experimental animal technology Co., Ltd.).

1.2 pharmaceuticals: heptapeptide GAGPHGG (self made, >98%); positive drug bifendate pills (Peking Union Pharmaceutical Factory).

1.3 principal reagents: kits of alanine aminotransferase (ALT), aspartate aminotransferase(AST), glutathion peroxidase(GSH-Px) and malondialdehyde (MDA) were all purchased from Nanjing Jiancheng Bioengineering Institute, and other agents were all analytical pure made in China. The equipments used included compact centrifuge (Sigma 1213), 722-type spectrophotometer (Xiamen Analytical Instrument Factory), and so on.

2. Methods

According to random number table, 60 male Kunming mice were divided into a normal control group, a model control group, a bifendate group, a heptapeptide large dose group and a heptapeptide small dose group, and the latter two groups were administered subcutaneously at 0.17 mg/kg and 0.085 mg/kg, respectively, once every two days for 7 d; the bifendate group was intragastric administered at 100 mg/kg once daily for 7 d; and the normal control group and model control group were administered subcutaneously with the same volume of physiological saline; after 1 h after the last administration, except for the normal control group, other groups were given olive oil solution comprising 0.15% carbon tetrachloride at 5 mL/kg by intraperitoneal injection. Each group was fasted but not restraint from water. Blood was taken from eyeball after 12 h, and the serum was separated for use. The mice were killed after the blood was taken, then dissected and the liver were taken out and homogenized for use. For mice from each group, the ALT, AST activities in the serum, and GSH-Px activity and MDA content in liver tissue were measured according to the kit instruction, and all data were expressed as mean±standard deviation (x±SD), and analysis of variance was used for the hypothesis test of mean value differences between each group.

3. Results 3.1 effect of the heptapeptide on serum ALT and AST activities

It can be seen from table 2 that compared with that of the model control group, the serum ALT, AST activities of the heptapeptide large dose group and the heptapeptide small dose group declined significantly, and the differences were significant (P <0.01).

TABLE 2

Effect of the heptapeptide on serum ALT and AST activities of mice with liver injury induced by carbon tetrachloride (x ± s, U/L)

| group | n | dosage (mg/kg) | ALT | AST |
|---|---|---|---|---|
| normal control group | 12 | — | 36.24 ± 9.62 | 141.36 ± 11.26 |
| model control group | 12 | — | 346.72 ± 46.17 | 286.78 ± 42.15 |
| heptapeptide group | 12 | 0.085 | 123.24 ± 19.73** | 186.97 ± 37.56** |
|  | 12 | 0.17 | 86.52 ± 28.72** | 148.62 ± 31.25** |
| biphenyl-dicarboxylate group | 12 | 100 | 92.36 ± 35.27** | 156.24 ± 34.12** |

Compared with control group, **P < 0.01

3.2 Effect of the heptapeptide on GSH-Px activity and the MDA content of liver tissue It can be seen from table 3 that the liver tissue GSH-Px activities of the heptapeptide large dose group and the heptapeptide small dose groups were significantly higher than that of the model control group, and the MDA content were significantly lower than that of the model control group. After comparison, the differences were significant(P<0.01).

TABLE 3

Effect of the heptapeptide on GSH-Px activity and the MDA content of liver tissue (x ± s, μmol/g)

| group | n | dosage (mg/kg) | GSH-PX | MDA |
|---|---|---|---|---|
| normal control group | 12 | — | 317.56 ± 26.52 | 1.82 ± 1.21 |
| model control group | 12 | — | 2.27 ± 14.71 | 11.52 ± 2.51 |
| heptapeptide group | 12 | 0.085 | 267.18 ± 32.13** | 6.48 ± 1.65** |
|  | 12 | 0.17 | 308.28 ± 38.54** | 2.75 ± 1.36** |
| biphenyldicarboxylate group | 12 | 100 | 296.82 ± 18.31** | 5.29 ± 1.25** |

Compared with control group, **P < 0.01

4. Conclusions: the heptapeptide can significantly inhibit the serum ALT and AST activities of mice with acute liver injury induced by carbon tetrachloride, and presents protection for the acute liver injury resulted from carbon tetrachloride.

Example 6 Experimental research on the anti-rat liver fibrosis effect of oligopeptide GAGPHGG 1. Materials 1.1 animals: healthy male SD rats(150±10 g, Beijing Vital River experimental animal technology Co., Ltd.).

1.2 pharmaceuticals: heptapeptide GAGPHGG (self made, >98%); positive drug Bifendate pills (Peking Union Pharmaceutical Factory).

1.3 principal reagents: kits of alanine aminotransferase (ALT), aspartate aminotransferase(AST), glutathion peroxidase(GSH-Px), malondialdehyde(MDA), TGF-βmRNA in-situ hybridization kits and TIMP- ELISA kits for rats were all purchased from Nanjing Jiancheng Bioengineering Institute, and other agents were all analytical pure made in China.

2. Methods: 48 rats were randomly divided into a control group, a model group, a heptapeptide large dose group and a heptapeptide small dose group, each group contains 12 rats. CCl4 was formulated into 40% solution with olive oil, and the solution was then injected subcutaneously to the animals at 5 ml/kg twice a week for 8 weeks; the intervention group with GAGPHGG was given the heptapeptide subcutaneously (the concentrations was 0.12 mg/kg and 0.06 mg/kg, respectively, once every two days, 8 weeks) while the model was setting up. The animals of each group were killed at 48 h after the last injection of CCl4, and then serum and liver tissue were taken for detection. The serum ALT, AST and TGFβ1 level were measured according to the kit instruction, and the liver tissue sample was fixed with neutral formalin solution and imbedded with paraffin. 5 ttm tissue section was made by using glass slide coated with polylysine, and it was then stained with HE and Masson triplication collogen for histopathological examination.

3. Results 3.1 Effect of the heptapeptide on the serum ALT and AST levels of rats with liver fibrosis It can be seen from table 4 that ALT and AST levels of the rats with liver fibrosis of the heptapeptide large dose group and the heptapeptide small dose group significantly declined compared with that of the model control group, and after comparison, the differences were significant ($P<0.01$).

TABLE 4

Effect of the heptapeptide on the serum ALT and AST levels of rats with liver fibrosis (x ± s, U/L)

| group | n | dosage (mg/kg) | ALT | AST |
|---|---|---|---|---|
| normal control group | 12 | — | 38.67 ± 8.46 | 85.63 ± 12.21 |
| model control group | 10 | — | 296.38 ± 76.82 | 484.51 ± 136.06 |
| heptapeptide group | 12 | 0.06 | 148.24 ± 32.52** | 180.35 ± 28.49** |
| | 12 | 0.12 | 96.37 ± 35.12** | 108.75 ± 42.21** |

Compared with control group, **$P < 0.01$ 3.2 Effect of the heptapeptide on the TGFβ1 and collogen area of liver tissue of rats with liver fibrosis It can be seen from table 5 that the serum TGFβ1 level of liver fibrosis rats induced by CCl4 increased significantly($P<0.01$), which indicates that the formation of liver fibrosis is accompanied with the increase of TGFβ1 synthesis, so as to promote the synthesis and deposit of liver collagen fibers; the serum TGFβ1 level of rats prophylactically treated with heptapeptide large dose decreased significantly(compared with model group $P<0.01$), and the mean area of liver collagen also decreased significantly (compared with model group $P<0.01$). That of heptapeptide small dose group had a decreasing trend, but not statistically significant.

TABLE 5

Effect of the heptapeptide on the TGFβ1 and collogen area of liver tissue of rats with liver fibrosis (x ± s)

| group | n | dosage (mg/kg) | TGFβ1 (mg/L) | collogen area ($\mu m^2$) |
|---|---|---|---|---|
| normal control group | 12 | — | 15.62 ± 6.59 | 66.28 ± 13.52 |
| model control group | 10 | — | 96.82 ± 16.32 | 632.57 ± 121.36 |
| heptapeptide group | 12 | 0.06 | 74.24 ± 18.58 | 380.82 ± 78.89 |
| | 12 | 0.12 | 32.65 ± 11.02** | 138.12 ± 62.58** |

Compared with control group, **$P < 0.01$

4. Conclusions: The heptapeptide GAGPHGG has some anti-liver fibrosis effect, and its anti-liver fibrotic mechanism needs further study.

Example 7

10 g heptapeptide GAGPHGG was taken, suitable excipients for injections (including freeze-dried powder injection and aseptic dispensing dry powder injection) were added to the heptapeptide, and injections were prepared according to the process for injections (including freeze-dried powder injection and aseptic dispensing dry powder injection).

Example 8

10 g heptapeptide GAGPHGG was taken, suitable excipients for tablets (including sustained release tablets and controlled release tablets, matrix tablets, coated tablets, dispersible tablets, and so on) were added, and then sublingual tablets or tablets were prepared according to the process for tablets(including sustained release tablets and controlled release tablets, matrix tablets, coated tablets, dispersible tablets, and so on).

Example 9

10 g heptapeptide GAGPHGG was taken, suitable excipients for capsules were added, and then enteric capsules or capsules were prepared according to the process for capsules.

Example 10

10 g heptapeptide GAGPHGG was taken, suitable excipients for emulsions (including micro emulsions, nanometer emulsions, and so on) were added, and then micro emulsions were prepared according to the process for emulsions(including micro emulsions, nanometer emulsions, and so on).

Example 11

10 g heptapeptide GAGPHGG was taken, suitable excipients for sustained release agent or controlled release agent were added, and then various kinds of sustained release agent and controlled release agent were prepared according to the process for sustained release agent or controlled release agent.

Example 12

10 g heptapeptide GAGPHGG was taken, suitable excipients for liposomes were added, and then various kinds of liposomes were prepared according to the process for liposomes.

The invention claimed is:

1. A synthesized oligopeptide, consisting of the amino acid sequence of SEQ ID NO: 1 (GAGPHGG), wherein one or more of the amino acid is D-type amino acid.

2. A pharmaceutical composition comprising the synthetic oligopeptide according to claim 1, and a pharmaceutically acceptable carrier.

3. A method for resisting HBV or liver fibrosis, which comprises administering the synthesized oligopeptide according to claim 1 as required in a pharmaceutically acceptable form every day.

* * * * *